United States Patent
Shoji et al.

(10) Patent No.: US 8,177,951 B2
(45) Date of Patent: May 15, 2012

(54) ELECTROPHORESIS APPARATUS AND PUMP MECHANISM USED IN THE SAME

(75) Inventors: Tomohiro Shoji, Hitachinaka (JP); Takashi Gomi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1031 days.

(21) Appl. No.: 12/153,395

(22) Filed: May 19, 2008

(65) Prior Publication Data

US 2008/0296161 A1    Dec. 4, 2008

(30) Foreign Application Priority Data

Jun. 1, 2007    (JP) ................................ 2007-146731

(51) Int. Cl.
*G01N 27/447* (2006.01)
(52) U.S. Cl. ....................... 204/604; 422/500
(58) Field of Classification Search .......... 204/601–604, 204/607; 417/48, 417; 435/287.1–288.7; 422/500, 501
See application file for complete search history.

(56) References Cited

U.S. PATENT DOCUMENTS

| | | | |
|---|---|---|---|
| 6,936,152 B2 | 8/2005 | Kojima et al. | |
| 7,005,052 B2 | 2/2006 | Shimizu et al. | |
| 2007/0175757 A1* | 8/2007 | Hanafusa et al. | 204/451 |

FOREIGN PATENT DOCUMENTS

| | | |
|---|---|---|
| JP | 2001-281221 | 10/2001 |
| JP | 2001-324473 | 11/2001 |
| JP | 2001-324475 | 11/2001 |

* cited by examiner

*Primary Examiner* — Alex Noguerola
*Assistant Examiner* — Gurpreet Kaur
(74) *Attorney, Agent, or Firm* — McDermott Will & Emery LLP (57) ABSTRACT

To obtain a stable pressure to inject polymer into a capillary array in order to shorten the injection time and raise the processing capacity of the apparatus.

Disclosed herein is an electrophoresis apparatus comprising one or more capillaries to be filled with an electrophoretic medium and a pump mechanism which can be connected to the capillaries for filling the capillaries with an electrophoretic medium. The pump mechanism comprises a plunger; a slider which is bonded to the plunger and moves together with the plunger; a spring which gives force to the slider; a cover which limits the range of displacement of the slider; and a linear motion system which is bonded to the cover and moves linearly, wherein the cover and the slider move as one body when the electrophoretic medium is taken to the plunger, and the plunger is pushed by the action of the spring when the electrophoretic medium is injected from the plunger into the capillaries.

7 Claims, 7 Drawing Sheets

ELECTROPHORESIS APPARATUS AND PUMP MECHANISM USED IN THE SAME

BACKGROUND OF THE INVENTION

1. Field of the Invention

The present invention relates to capillary electrophoresis apparatus and pump mechanisms suitable for such electrophoresis apparatus. In particular, the invention relates to an electrophoresis apparatus where a capillary or a capillary array is filled with a gel or a liquid polymer solution which serves as a separating or electrophoretic medium and a pump mechanism suitable for such electrophoresis apparatus.

2. Description of the Related Art

Capillary electrophoresis is in widespread use as a technique to separate/analyze deoxyribonucleic acids (DNAs) and many other biological samples. One of its technical advantages is the superior heat radiation ability due to the capillary's surface area to volume ratio. This heat radiation ability has realized high speed and high resolution separation of analytes by high voltage-used electrophoresis.

Another advantage of the capillary electrophoresis is that analysis can easily be multiplexed by using multiple capillaries at the same time. Multi-capillary high throughput electrophoresis apparatus are put to practical use.

In JP-A-2001-281221 and JP-A-2001-324473, an electrophoresis apparatus using a capillary array composed of 16 capillaries is disclosed. Each capillary is a thin tube with an inner diameter of several ten to several hundred $\mu$m. It is made mainly of quartz and coated externally with a polyimide film of several ten $\mu$m in thickness for the purpose of enhancement in mechanical strength. To perform electrophoresis, the capillaries are filled in advance with a component which serves as a sample separation medium.

Although non-liquid cross-linked polymers were used as electrophoretic separation media in the past, it is common in these days to use non-cross-linked liquid polymer solutions since they are superior in productivity and performance stability. JP-A-2001-281221 discloses a pump which fills the capillaries with a gel or polymer as a sample separation medium. This disclosed pump mechanism is a glass syringe. The currently available electrophoresis apparatus include such a one as provided with a pump mechanism which drives a sapphire plunger.

In JP-A-2001-324475, the length or number of capillaries is changed according to the type of analysis and the throughput required by the user. Relatively long capillaries are used in resolution-critical applications where, for example, DNA analytes with several hundred to one thousand bases are separated by the number of bases in steps of one base. Relatively short capillaries are used when resolution is not so critical as analysis speed. Large scale users such as genome analysis centers which deal with many samples demand high throughput while laboratory-level small-scale users may not be dissatisfied with low throughput.

In addition, JP-A-2001-324475 discloses a capillary array which can be replaced by the user. This capillary array is secured at three points, namely its sample introduction end, optical detection section and polymer solution injection end. The polymer solution injection end of the capillary array is connected to the pump mechanism of the electrophoresis apparatus.

Specifically, each of the electrophoresis apparatus disclosed in JP-A-2001-281221, JP-A-2001-324473, and JP-A-2001-324475 uses a 16-capillary array. At the polymer solution injection end, 16 capillaries are tied up in a bundle of about 3.5 mm in diameter. The polymer solution injection end is inserted horizontally into an acrylic block and fixed airtightly by means of a sleeve and locking screws. A reservoir syringe to reserve polymer solution and an injection syringe to inject polymer solution at high pressure into the capillaries are attached to the block. Both syringes communicate with the capillary array through the internal flow passage of the block.

Further, there is provided a second block to which a reservoir to contain buffer solution can be attached. The first block to which the capillary array is attached is connected with this second block by a tube. The capillary array communicates with the buffer solution supplied to the second block via the flow passage formed in the first block, the tube and the flow passage formed in the second block. In addition, since an electrode to serve as an anode is inserted in the buffer solution supplied to the second block, the flow passage from the capillary array to the buffer solution constitutes an electrophoretic passage when a voltage is applied for electrophoresis.

In an electrophoresis apparatus, it is common to inject high viscosity liquid polymer at high pressure into capillaries whose inner diameter is several ten to several hundred microns. If the pressure is low, polymer injection is time-consuming, which lowers the processing capacity of the apparatus. Further, polymer injection is done each time measurement is newly started in order to prevent the variation and deterioration of the performance. To shorten the time required for analysis or raise the processing capacity of the apparatus, a pump mechanism which can stably generate high pressure is needed.

JP-A-2001-281221 discloses a method of utilizing the stalling torque of the motor which generates polymer injection pressure. This method utilizes the DC motor's nature that as the torque grows, the motor decreases its rotation speed and finally stops.

Specifically, the following steps are repeated to control the pressure. (1) If the internal pressure of the syringe rises to a target level, the DC motor stops due to the increased load torque. (2) If the internal pressure of the syringe falls due to progress of polymer penetration into the capillaries, the motor starts rotating. In this case, the current to be supplied to the motor is adjusted so that the motor stops at the target pressure to control the torque characteristics. The target pressure is determined so as not to cause leakage or damage in the flow lines. As well, there exists electrophoresis apparatus where the same pressure control method is implemented by using a stepping motor.

SUMMARY OF THE INVENTION

To raise the processing capacity of an electrophoresis apparatus where a gel or a liquid polymer solution must be injected as a separation medium into capillaries or a capillary array, it is necessary to make the pressure to inject polymer into the capillaries as high as possible. Practically, however, the polymer injection pressure is set lower than the maximum pressure which can be endured by the flow lines of the apparatus. In addition, when the pump pressure may fluctuate due to characteristics of the pump drive system or change with time, the working pressure must be set by taking these factors into consideration so that the pressure never exceeds the maximum allowable pressure of the apparatus. That is, the working pressure must be set lower than the maximum allowable pressure of the flow lines by the possible maximum deviation of the working pressure at least. Thus, a less-deviating pump system can set the working pressure nearer to the maximum pressure endurable by the flow lines and, as a result of the raised working pressure, can advantageously realize an apparatus superior in processing capacity.

In the above-mentioned apparatus, the pressure is controlled by utilizing torque characteristics of the motor. Torque characteristics of the motor change depending on the ambient temperature. Torque characteristics of the motor, namely the stalling torque and starting torque have variations in reproducibility. These variations in the motor torque characteristics result in a deviation of the pressure. Further, the frictional force in the lead screw section which converts the motor's rotation to linear motion may change, causing a deviation of the pressure. In the above-mentioned apparatus, the preset pressure is determined by subtracting at least these deviations from the withstand pressure of the flow lines.

Further, since motors have variations in characteristics, it is necessary to compensate for such variations on an each motor basis by adjusting the magnitude of current. Such an adjusting work may deteriorate productivity.

Further, if the amount of polymer treated in the system is small, the load torque does not show a large change when the pressure rises since the diameter of the plunger is small. If the change of the load torque is small, pressure control by the above-mentioned method is difficult.

Therefore, it is an object of the present invention to provide an electrophoresis apparatus which is improved in processing capacity by obtaining a stable pressure to inject polymer into the capillary array and consequently reducing the injection time, and it is another object of the present invention to provide a pump mechanism capable of stably generating high discharge pressure.

The present invention provides an electrophoresis apparatus comprising one or more capillaries to be filled with an electrophoretic medium and a pump mechanism which can be connected to the capillaries for filling the capillaries with an electrophoretic medium, the pump mechanism comprising: a plunger; a slider which is bonded to the plunger and moves together with the plunger; a spring which gives force to the slider; a cover which limits the range of displacement of the slider; and a linear motion system which is bonded to the cover and moves linearly; wherein the cover and the slider move as one body when the electrophoretic medium is taken to the plunger, and the plunger is pushed by the action of the spring when the electrophoretic medium is injected from the plunger into the capillaries.

In addition, the present invention provides a pump mechanism comprising: a plunger for taking in or delivering an electrophoretic medium; a slider which is bonded to one end of the plunger; a linear motion system; a compressed spring inserted between the slider and a junction of the linear motion system; a cover which coaxially supports the slider, the spring and the junction so that the slider and the spring can move axially, the cover having one end fixed to the junction; and detection means to detect the position of the slider relative to the cover; wherein the cover and the plunger move in one direction as one body when the electrophoretic medium is taken in, and the spring pushes the plunger in the opposite direction when the electrophoretic medium is delivered.

An apparatus according to the present invention can provide improved processing capacity by reducing the injection time since it is possible to obtain a stable pressure to fill the capillary array with polymer. Since the plunger is pushed by the action of a spring, it is possible to eliminate the pressure deviation attributable to above-mentioned variations in characteristics among motors.

BRIEF DESCRIPTION OF THE DRAWINGS

Other objects and advantages of the invention will become apparent from the following description of embodiments with reference to the accompanying drawings in which.

DETAILED DESCRIPTION OF THE PREFERRED EMBODIMENTS

The present invention relates to an electrophoresis apparatus and a pump mechanism where a spring is used to control the pumping pressure to fill the capillaries with polymer. Specific embodiments of the present invention are described below as examples.

Preferably, the above-mentioned electrophoresis apparatus is such that the spring is set shorter than the natural length thereof when installed in the pump mechanism. It is also preferable that above-mentioned electrophoresis apparatus is such that the pump mechanism further comprises a detection rod bonded to the slider and a sensor to detect the detection rod; and the pump mechanism is constructed so that the sensor detects the detection rod when the slider has reached a position at which injection of the electrophoretic medium is to be completed. It is also preferable that the above-mentioned electrophoresis apparatus is such that the pump mechanism further comprises a slit plate bonded to the slider and an encoder to detect slits in the slit plate and the encoder is attached to the cover and detects the position of the slider relative to the cover.

An electrophoresis apparatus according to another aspect of the present invention comprises a capillary array having plural capillaries to be filled with an electrophoretic medium and a pump mechanism which can be connected to one of each of the capillaries for filling the capillaries with the electrophoretic medium, wherein: the pump mechanism comprises a plunger to take in or deliver the electrophoretic medium, a slider which is bonded to one end of the plunger, a linear motion system, a compressed spring inserted between the slider and the junction of the linear motion system, a cover which coaxially supports the slider, the spring and the junction so that the slider and the spring can move axially and has one end fixed to the junction, and detection means for detecting the position of the slider relative to the cover; the cover and the plunger move in one direction as one body when the electrophoretic medium is taken into the pump mechanism; and the spring pushes the plunger when the electrophoretic medium is injected into the capillaries.

Preferably, the above-mentioned electrophoresis apparatus is such that the detection means comprises a detection object bonded to the slider and a sensor to detect the position of the detection object.

It is also preferable that the detection means comprises: a slit plate which has slits spaced in the axial direction of the cover and is bonded to the slider; and an encoder which is attached to the cover to detect slits in the slit plate. It also preferable that the sensor is constructed so that the detection rod is detected when the slider has reached a position at which injection of the electrophoretic medium is to be completed.

Preferably, the above-mentioned pump mechanism is such that the detection means comprises a detection object bonded to the slider and a sensor to detect the position of the detection object. It is also preferable that the detection means comprises: a slit plate which has slits spaced in the axial direction of the cover and is bonded to the slider; and an encoder which is attached to the cover to detect slits in the slit plate. In addition, the sensor may be constructed so that the detection object is detected when the slider has reached a position at which polymer injection is to be completed.

Preferably, in the above-mentioned electrophoresis apparatus, the force to push the plunger is controlled by the action of the spring inserted between the electric liner motion section and the plunger. In order to attain a desired characteristic, it is preferable that a deformed low rigidity spring is installed. Using such a low rigidity spring suppresses the decrease of the pressure attributable to the spring characteristic.

Preferably, when the electric liner motion section moves in the direction to take in polymer, the electric liner motion section and the plunger move as one body. Since this makes it possible to accurately control the travel speed of the plunger when the plunger is pulled to take in polymer, it is possible to prevent air bubble from penetrating from the piping junctions, etc.

It is also preferable that a detection plate is set to the slider so that an optical detector detects the detection plate when the slider has reached a certain position. It is also preferable that the detection plate is detected when the plunger is fully pushed. This makes it possible to recognize that injection of the polymer or electrophoretic medium is complete and automatically start the subsequent operation.

In addition, the present invention is structurally immune to fluctuations of the frictional force in the lead screw section. Since the force given by the spring is dependent only upon the characteristics and deformation of the spring, the present invention does not require calibration on each apparatus basis. The present invention can cope with a wide range of plunger sizes since there a variety of springs are available. In addition, since the present invention does not need pressure sensors, it is possible to suppress the costs of the electrophoresis apparatus and pump mechanism.

Embodiments of the present invention will be described below in detail with reference to the drawings.

Embodiment 1

Figure 1:
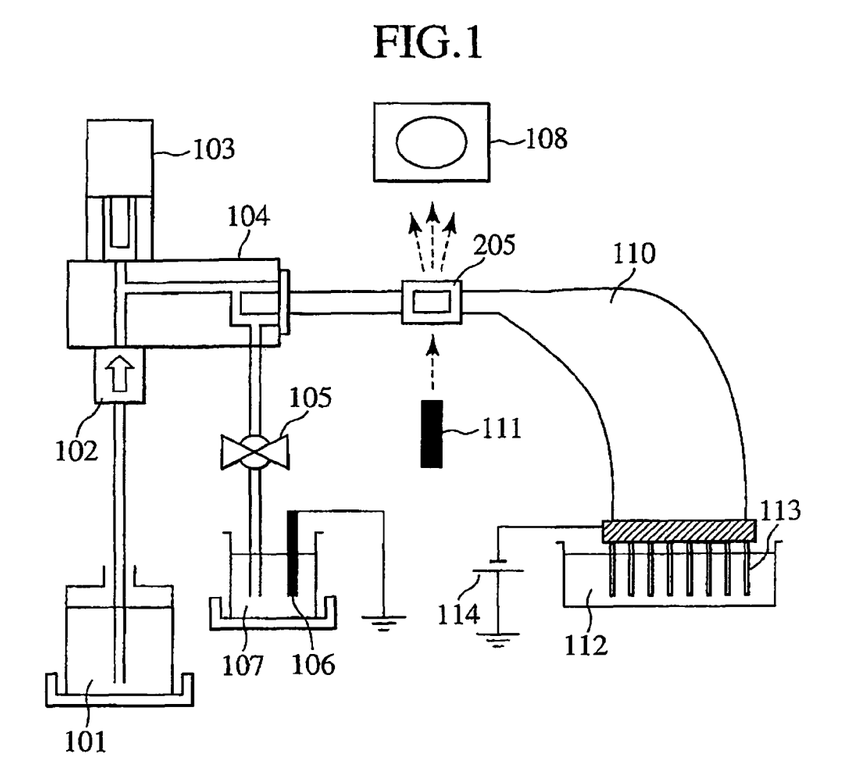
FIG. 1 schematically shows the basic configuration of an electrophoresis apparatus provided with a polymer injection mechanism.

FIG. 1 schematically shows the basic configuration of a capillary electrophoresis apparatus. The capillary electrophoresis apparatus includes a capillary electrophoresis section and an optical detection section. The capillary electrophoresis section includes capillaries (thin tubes with an internal diameter of several ten to several hundred ▫m) which are filled with an electrophoretic medium, namely a high viscosity polymer solution (hereinafter, referred to as the polymer). The optical detection section detects samples subjected to electrophoresis separation. The capillary electrophoresis apparatus also includes a flow passage block 104 and a polymer injection mechanism. The flow passage block 104 constitutes a junction flow passage which can communicate with the capillaries. The polymer injection mechanism is a pump which can fill the capillaries with the electrophoresis medium. Through operation of the pump 103, the polymer injection mechanism sucks the polymer from a bottle (hereinafter, referred to as the polymer bottle) 101 containing the polymer and injects the polymer into the capillary array composed of, for example, 96 capillaries.

The following schematically describes the configuration of the apparatus. One end (sample injection end) of the capillary array 110 composed of 96 capillaries is immersed into the buffer in a buffer reservoir 112 whereas the other end is connected to the flow passage block 104. The flow passage block 104 is connected to not only the capillary array 110 but also the polymer bottle 101 and another buffer reservoir 107. The flow passage block 104 has an internal flow passage formed to communicate with them. Between the flow passage block 104 and the polymer bottle 101, there is disposed a check valve 102 to prevent the polymer from flowing back into the polymer bottle 101 when the polymer is injected into the capillary array 110 from the pump 103.

The polymer bottle 101 has a sufficient capacity for continuous operation. The structure is also designed to have a sufficient opening around the exhaust valve or the tube insertion port so that the bottle's internal pressure does not become negative. In addition, the polymer bottle 101 is disposed in a lower position than the buffer reservoir 107 so that the pressure due to the level difference does not force the polymer to flow back into the buffer reservoir 107 from the polymer bottle 101. The check valve 102 can be operated to prevent the polymer or the buffer solution from flowing into the polymer bottle 101.

Between the buffer reservoir 107 and the flow passage block 104, there is disposed an electrically operated buffer valve 105. To inject the polymer into the capillaries of the capillary array 110, the buffer valve 105 is closed to close the flow passage between the capillary array and the buffer reservoir. During electrophoresis, the buffer valve 105 is opened to open the flow passage so that the capillary array communicates with the buffer reservoir.

Figure 2:
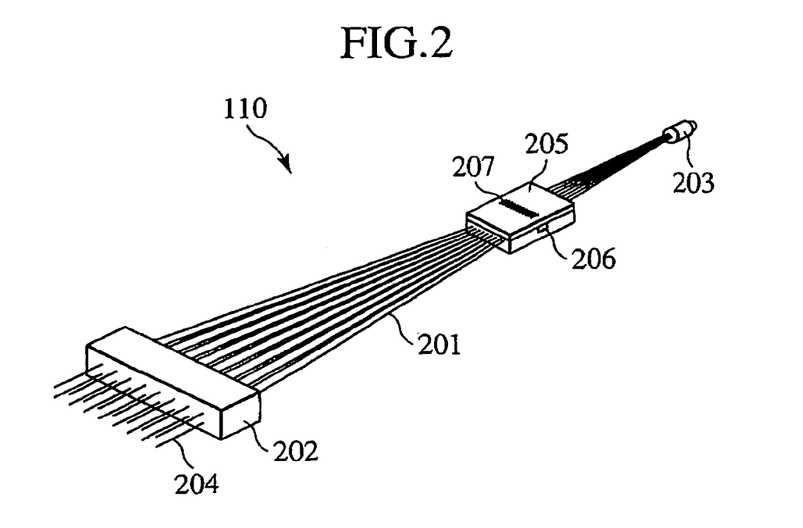
FIG. 2 schematically shows the basic configuration of a capillary array.

FIG. 2 schematically shows an example of the capillary array 110. Each of the capillaries constituting the capillary array has an outer diameter of 0.1 to 0.7 mm and an inner diameter of 0.02 to 0.5 mm and is externally coated with polyimide resin. Each capillary itself is a quartz pipe. Plural capillaries (16 capillaries in this example) are arrayed to form a capillary array. The capillary array 110 has a load header 202, a detection section (window unit) 205 and a capillary head 203. From sample vials each containing a fluorescently labeled DNA sample or the like, the load header 202 electrically takes samples into the capillaries. In the detection section 205, the capillaries 201 from the load header 202 are arrayed and secured in the order of sample numbers. The capillaries from the detection section 205 are tied and fixed to each other at the capillary head 203. The sample injection tips projecting from the load header 202 are provided with hollow electrodes 204 to apply an electrophoretic voltage to the capillaries. The detection section (window unit) 205 has openings 206 and 207. The opening 206 is for irradiating the retained capillary array from a side whereas the opening 207 is for bringing out the light emitted from the capillaries.

The capillary array 110 shown in FIG. 2 is such that the hollow electrodes 204 and the sample injection tips of the capillaries 201, which are projected from the load header 202, are immersed in a plurality of sample tray wells filled with fluorescently labeled DNA samples whereas the capillary head 203 at the other end is hermetically attached to the flow passage block 104 filled with the polymer. Between an electrode 106 immersed in the buffer reservoir 107 which is connected to the flow passage block 104 and the hollow electrodes 204 of the load header 202, a high voltage in the order of several kV is applied from a high voltage power source 114. Consequently, samples in sample vials (omitted in the illustration) are electrostatically injected into the respective capillaries of the capillary array.

Then, the sample injection tips of the capillary array 110 are immersed in the buffer reservoir 112 as shown in FIG. 1. In each capillary, a sample injected electrostatically thereinto is electrophoretically separated. Although omitted in FIG. 1, an auto sampler is provided which carries the sample vials and the buffer reservoir 112 to the sample injection tips of the capillary array 110.

Laser light emitted from a laser light source 111 is guided to the detection section (window unit) 205 by an excitation optical system. Irradiated with the excitation light, the samples migrating there in the capillaries emit fluorescence or signal light for detection by a light detector 108 via a detection optical system. The capillary array 110 is an exchangeable component. According to the purpose of use, the user exchanges the capillary array for an appropriate one differing in the number/length of capillaries. Exchange is also made if the capillary array is deteriorated due to contamination or the like. Note that the apparatus configuration indicated here is one example and does not impose conditions or restrictions on the present invention.

Figure 3:
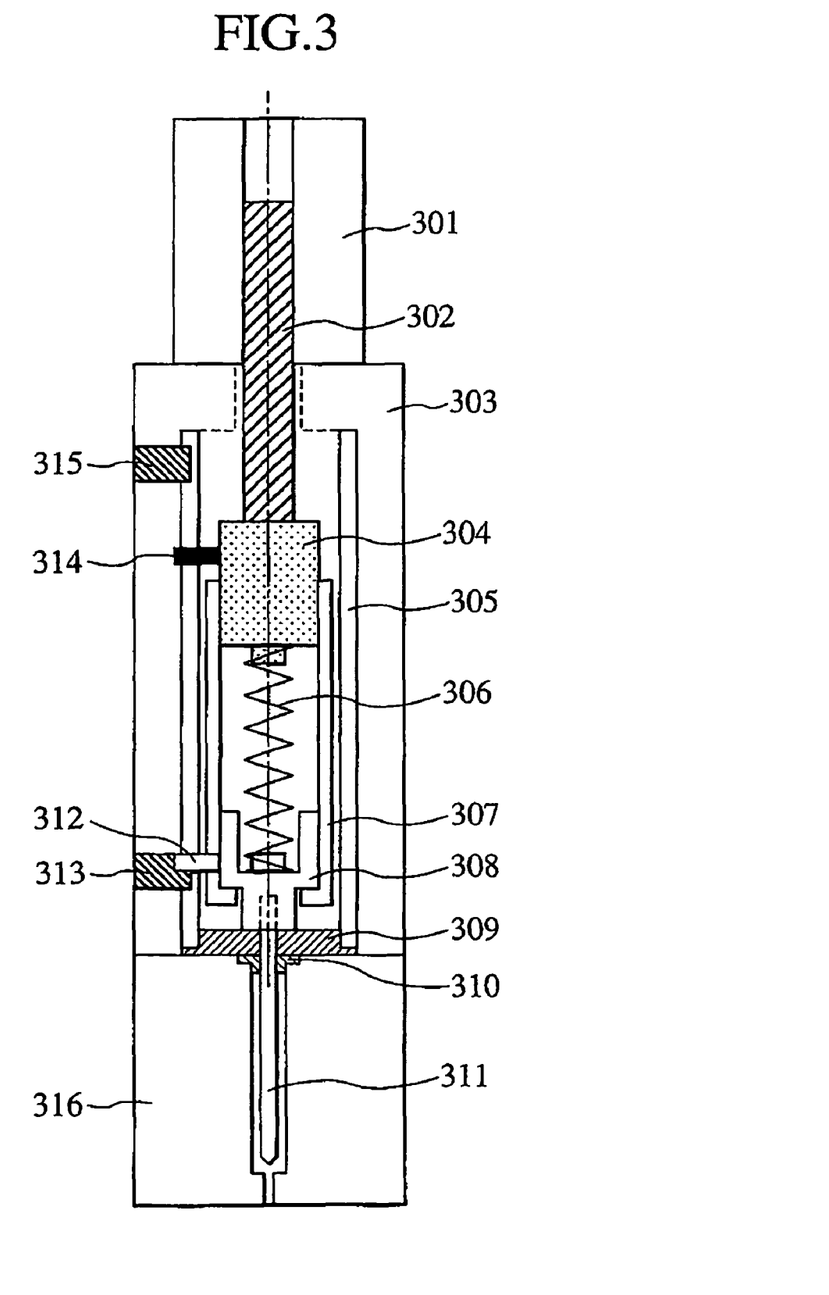
FIG. 3 schematically shows a plunger drive structure according to a first embodiment.

FIG. 3 schematically shows the plunger drive structure of the pump mechanism in the present embodiment. This pump mechanism serves as the pump 103 of FIG. 1. Rotating according to the number of pulses entered, a stepping motor 301 moves a lead screw 302 linearly or determines its position. An adapter 304 is bonded to one end of the lead screw 302 and coupled with a cover 307. The lead screw 302 and adapter 304 are collectively an example of a linear motion system. Inside the cover 307, a spring 306 and a slider 308 are set in a line. The slider 308 can move linearly inside the cover 307. The spring 306 deforms to follow the movement of the slider 308. The displacement of the slider 308 in the direction of a plunger 311 is limited by the cover 307. The plunger 311 is provided in a pump head 316. It is desirable that a spring having as small a spring constant as possible be compressed and incorporated as the spring 306. The reason will be described later.

Since the plunger 311 is combined with the slider 308, the plunger 311 and the slider 308 move as one body. The slider 308 is provided with a detection rod 312. When the plunger 311 is fully pressed by the slider 308, the detection rod 312 is detected by a first sensor 313 fixed to a frame 303. The adapter 304 is provided with a second detection rod 314. When the adapter 304 reaches the limit displacement position, the detection rod is detected by a second sensor 315 fixed to the frame 303.

At the above-mentioned limit position, a polymer intake operation is complete. The plunger 311 is inserted into the chamber part of the pump head 316 via a seal 310 which encloses the polymer. In contact with the polymer, the plunger 311 conveys the force of the spring 306 to the polymer via the slider 308.

The pump head chamber communicates with the flow passage block 104. Alternatively, the pump chamber may be formed within the flow passage block. In either case, the pump chamber communicates with the polymer bottle 101 and the capillary array 110. The frame 303 and the pump head 316 are combined so that a seal pusher support 305 presses the seal 310 via a seal pusher 309.

Figure 4A:
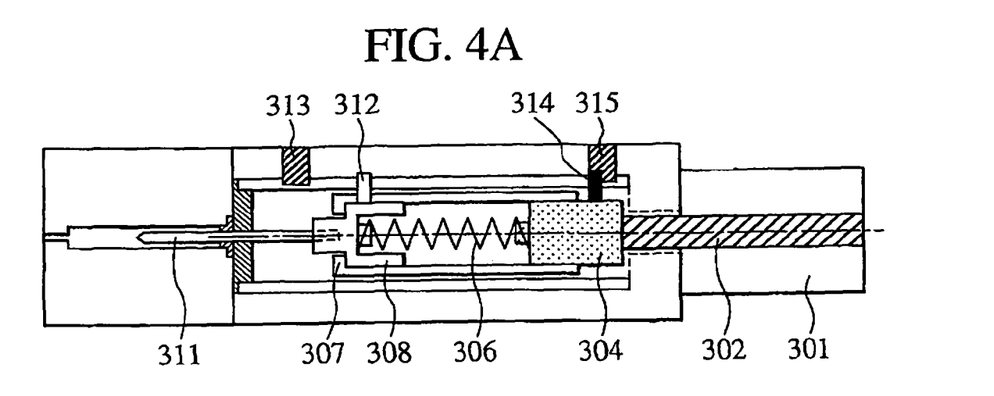
FIGS. 4A to 4C schematically show how the drive system of the first embodiment behaves to inject polymer.
Figure 4B:
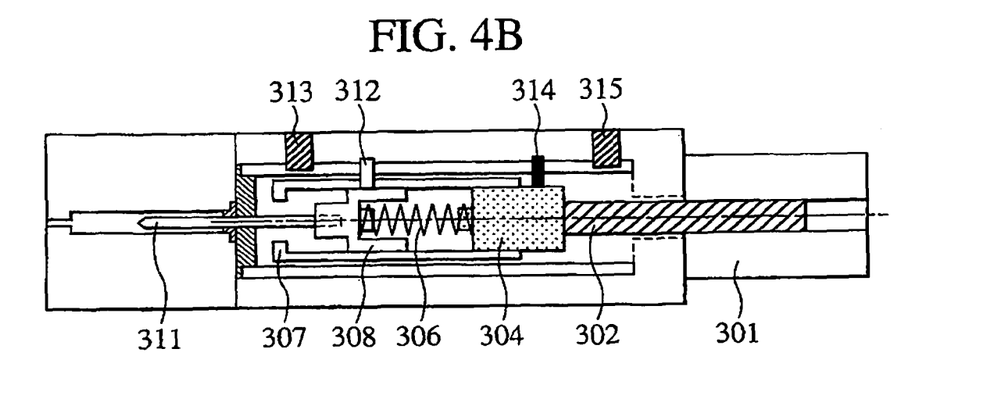
Figure 4C:
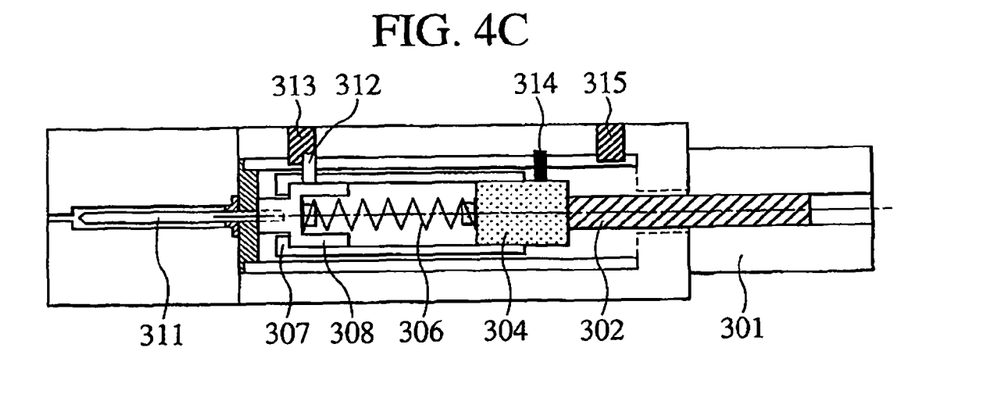

The following describes the procedure to be followed to inject the polymer. Shown in FIGS. 4A to 4C is the positional relation between the slider 308 and the cover 307 at each point. Note that in the following description, the motor's rotation direction to push the plunger into the plunger is expressed as normal while the direction to pull the plunger is reverse.

Initially, a valve 105 in FIG. 1 is closed. Then, in order to take in the polymer from the polymer bottle 101, the stepping motor 301 is reversely rotated to pull the plunger 311 until the second detection rod 314 is detected by the second sensor 315 as shown in FIG. 4A. During this step, the slider 308 moves together with the cover 307, the adapter 304 and lead screw 302 since the slider 308 is held by the cover 307.

The travel speed of the plunger 311 is determined by the rotation speed of the motor 301. This plunger travel speed is set so as not to suddenly make negative the internal pressure of the pump. Otherwise, air would be taken in from flow passage connections, etc. The amount of polymer taken in by this step is larger than the amount of polymer to be delivered by one polymer injection step. This makes it possible to complete the injection operation by a stroke of the plunger. Alternatively, taking in a small amount of polymer and injecting it may be repeated alternately as many times as required to fill the capillaries with polymer.

Further, the present embodiment may be such that the motor is given a certain number of pulses to take in a required amount of polymer after the polymer injection operation is completed, that is, after the first detection rod 312 is detected by the first sensor 313. In this case, the second sensor 315 and the second detection rod 314 are not necessary.

Then, the polymer is injected into the capillaries. When the polymer intake operation is complete, the slider 308 is in contact with the cover 307 as shown in FIG. 4A. The stepping motor 301 is rotated normally to move the lead screw 302, the adapter 304 and the cover 307 until the polymer injection end position is reached. During this process, the cover 307, the adapter 304 and the lead screw 302 travel as one body (hereinafter, "the cover 307, the adapter 304 and the lead screw 302 travel as one body" is expressed simply as "the cover 307 travels"). While the cover 307 travels depending on the motor's rotation speed, the slider 308 travels depending on the rate of polymer injection into the capillaries not on the motor's rotation.

In the present embodiment, the motor rotation speed is set so that the cover 307 travels ten or more times faster than the slider 308. Thus, the spring 306 exhibits a deformation associated with the difference of displacement between the slider 308 and the cover 307 (FIG. 4B) and the deformed spring 306 applies pressure to the polymer via the slider 308 and the plunger 311. The slider 308 travels with the progress of polymer injection into the capillaries and stops to complete the polymer injection when the slider 308 comes in contact with the cover 307 (FIG. 4C). That is, this mechanism is designed so that after the polymer injection operation is started, the cover 307 immediately reaches the polymer injection end position and the slider 308 gradually follow it depending on the polymer injection rate. By the first sensor 313 disposed to detect the detection rod 312 attached to the slider 308, it is possible to electrically detect the completion of the polymer injection operation.

Alternatively, the motor may be rotated for a certain polymer injection rate. In this method, however, the injection operation is normally completed even if the flow passage has a leak somewhere. In the case of the above-mentioned method, it is possible to judge whether the structure is leak-free by, for example, measuring the time it takes to complete the polymer injection after the injection is started since the polymer injection completes abnormally earlier if there is a leak. Finally, the valve 105 is opened in preparation for electrophoresis.

The following provides a description of how to select a spring suitable for the present embodiment. In the present embodiment, moving the cover 307 immediately maximizes the compression and pressure of the spring. In the subsequent profile, the deformation and pressure of the spring 306 gradually decrease as the plunger 311 moves. Preferably, the pressure is made as large as possible within the allowable range of the apparatus and as constant as possible.

In order to reduce fluctuations of the pressure depending on the plunger position, it is preferable to use a low rigidity spring. To attain a required pressure with a low rigidity spring, it is necessary to enlarge the deformation of the spring. Therefore, the low rigidity spring used in the present embodiment is such in size that the spring is deformed as required when set in the cover 307. This initial deformation of the incorporated spring is further enlarged additively when the polymer is injected.

As mentioned above, the present embodiment forces the spring to have another deformation corresponding to the difference of displacement between the cover 307 and the slider 308 when the polymer is injected. Thus, the maximum allowable deformation of the selected spring is required to be larger than the total deformation.

Figure 5:
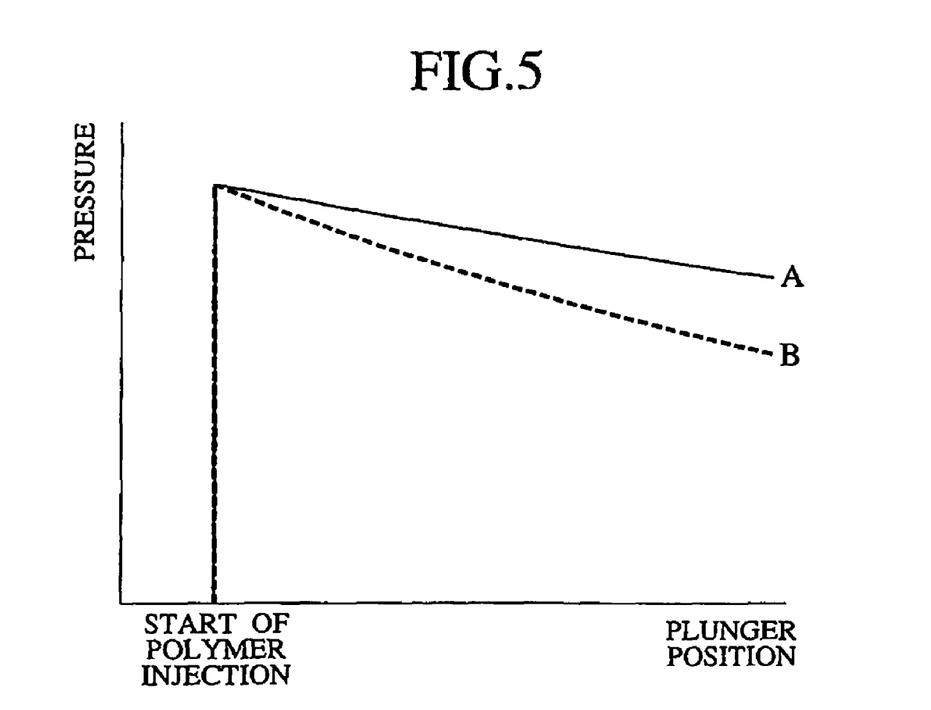
FIG. 5 schematically shows how the pressure changes with time in the first embodiment.

FIG. 5 schematically shows how the pressure changes with time when the polymer is injected in this method. In the figure, two type of springs differing in the spring constant are covered. A and B indicate how the pressure changes with a low rigidity spring and a high rigidity spring, respectively. Although both shows the same pressure when the polymer injection is started, the low rigidity spring can suppress the pressure change more than the high rigidity spring. Thus, use of a lower rigidity spring is more advantageous to raise the polymer injection speed since the average pressure is enlarged.

Embodiment 2

Figure 6:
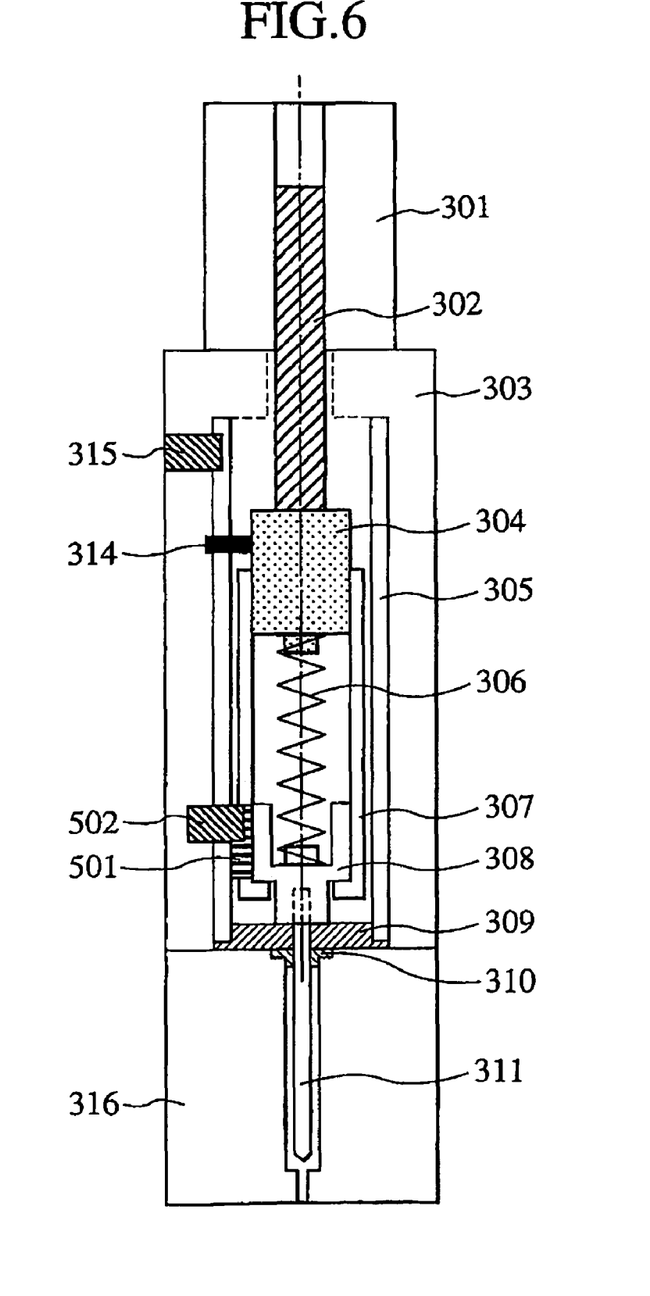
FIG. 6 schematically shows a plunger drive structure according to a second embodiment.

FIG. 6 schematically shows another plunger drive structure embodiment. Each component identical to the corresponding one in FIG. 3 is given the same reference numeral and description thereof is omitted unless necessary. The present embodiment is different from the aforementioned embodiment 1 in that a slit plate 501 having plural slits, not a detection rod, is attached to the slider 308 and the first sensor 313 is a slit counting encoder 502 attached to the cover 307 not the frame 303. Thus, control is possible to suppress the change of the pressure attributable to characteristics of the spring. This is described below in detail.

Figure 7A:
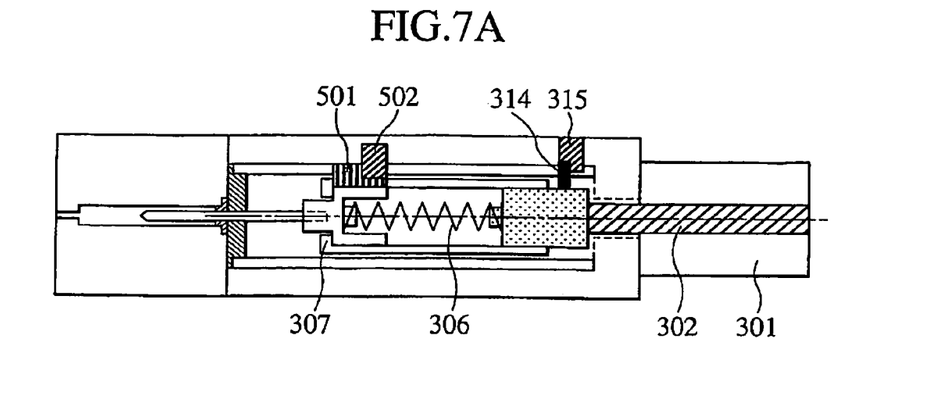
FIGS. 7A to 7C schematically show how the drive system of the second embodiment behaves to inject polymer.
Figure 7B:
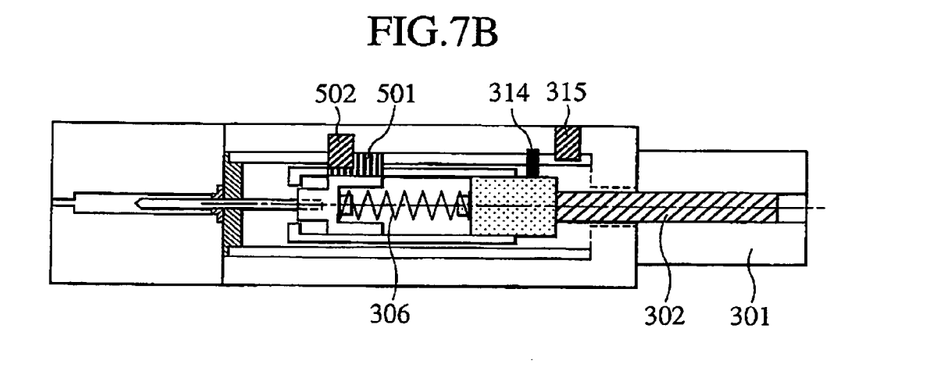
Figure 7C:
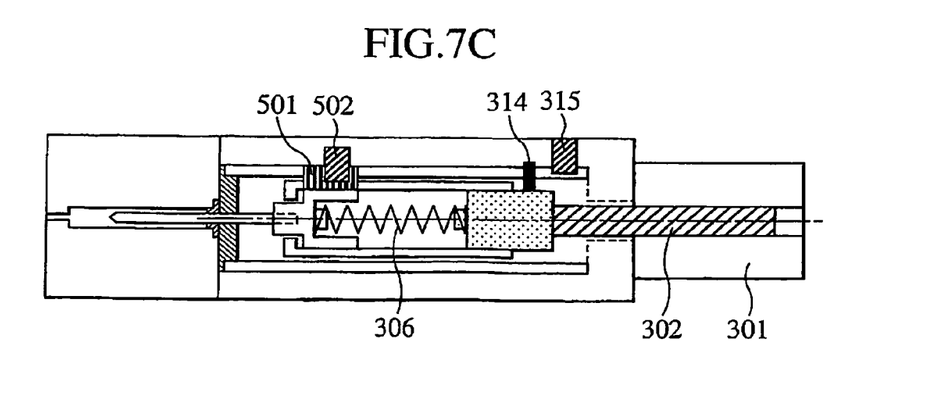

FIGS. 7A to 7C show positional relations between the slider 308 and the cover 307 when polymer is injected in the present embodiment. Initially, polymer is taken in from the polymer bottle through the same procedure as in the first embodiment FIG. 7A. Then, unlike the first embodiment in which the cover 307 is moved to the polymer injection end position without stopping, the cover 307 is moved a little toward the final position FIG. 7B. For example, this displacement may be about one tenth of the total displacement. After the cover 307 is moved a little, the slider 308 moves to follow it according to the polymer injection rate as in the first embodiment. The changing relative distance between the cover 307 and the slider 308 continues to be detected by the encoder 502.

When the relative distance of the moving slider 308 from the cover 307 is about to become equal to the initial distance FIG. 7C, the cover 307 is moved again a little. Such a small relative distance between the cover 307 and the slider 308 can be detected by the encoder 502. This operation is repeated until the cover 307 and the slider 308 reach the polymer injection end position. The point is that the cover 307 is moved again before the initial positional relation is restored between the cover 307 and the slider 308, that is, before the slider 308 comes in contact with the cover 307. If the slider 308 comes in contact with the cover 307, the force of the spring is not propagated to the polymer, resulting in a sharp decrease of the pressure. At the polymer injection end position, however, the slider 308 comes in contact with the cover 307. The displacement of the cover 307 is controlled by the number of pulses entered to the stepping motor 301.

This method is characterized in that the deformation of the spring is smaller than in the first embodiment. In the first embodiment, since the deformation of the spring is equal to the stroke required to complete the polymer injection, a pressure decrease associated with this stroke occurs. In the second embodiment, the deformation of the spring may be made smaller to suppress the pressure decrease attributable to the feature of the spring. In the second embodiment, since the deformation of the spring is small during polymer injection, the spring is deformed almost as required when installed in the apparatus.

Figure 8:
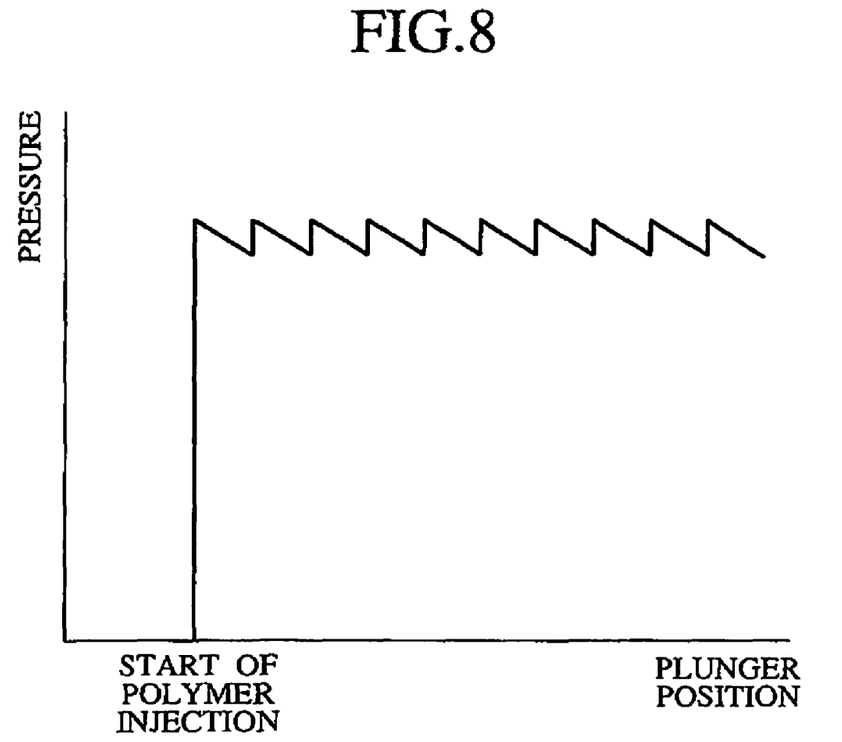
FIG. 8 schematically shows how the pressure changes with time in the second embodiment.

During polymer injection in the second embodiment, the pressure changes as shown in FIG. 8. This cyclic pressure change is attributable to each above-mentioned timing at which the cover 307 is moved.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An electrophoresis apparatus comprising:
    one or more capillaries to be filled with an electrophoretic medium; and
    a pump mechanism which can be connected to the capillaries for filling the capillaries with an electrophoretic medium, the pump mechanism comprising:
    a plunger;
    a slider which is bonded to the plunger and moves together with the plunger;
    a spring which gives force to the slider;
    a cover which limits the range of displacement of the slider; and
    a linear motion system which is bonded to the cover and moves linearly;
    wherein:
        the cover and the slider move as one body when the electrophoretic medium is taken to the plunger,
        the plunger is pushed by the action of the spring when the electrophoretic medium is injected from the plunger into the capillaries,
        the pump mechanism further comprises a slit plate bonded to the slider and an encoder to detect slits in the slit plate; and
        the encoder is attached to the cover and detects the position of the slider relative to the cover.

2. An electrophoresis apparatus comprising:
    a capillary array having plural capillaries to be filled with an electrophoretic medium; and
    a pump mechanism which can be connected to one end of each of the capillaries for filling the capillaries with the electrophoretic medium, the pump mechanism comprising:
    a plunger for taking in or delivering the electrophoretic medium;
    a slider which is bonded to one end of the plunger;
    a linear motion system;
    a compressed spring inserted between the slider and a junction of the linear motion system;
    a cover which coaxially supports the slider, the spring and the junction so that the slider and the spring can move axially, the cover having one end fixed to the junction; and
    detection means for detecting the position of the slider relative to the cover;
    wherein:
        the cover and the plunger move in one direction as one body when the electrophoretic medium is taken into the pump mechanism,
        the spring pushes the plunger when the electrophoretic medium is injected into the capillaries, and the detection means comprises a detection object bonded to the slider and a sensor to detect the position of the detection object.

3. An electrophoresis apparatus comprising:
a capillary array having plural capillaries to be filled with an electrophoretic medium; and
a pump mechanism which can be connected to one end of each of the capillaries for filling the capillaries with the electrophoretic medium, the pump mechanism comprising:
a plunger for taking in or delivering the electrophoretic medium;
a slider which is bonded to one end of the plunger;
a linear motion system;
a compressed spring inserted between the slider and a junction of the linear motion system;
a cover which coaxially supports the slider, the spring and the junction so that the slider and the spring can move axially, the cover having one end fixed to the junction; and
detection means for detecting the position of the slider relative to the cover;
wherein:
the cover and the plunger move in one direction as one body when the electrophoretic medium is taken into the pump mechanism; and the spring pushes the plunger when the electrophoretic medium is injected into the capillaries, and
the detection means comprises: a slit plate which has slits spaced in the axial direction of the cover and is bonded to the slider; and an encoder which is attached to the cover to detect slits in the slit plate.

4. An electrophoresis apparatus comprising:
a capillary array having plural capillaries to be filled with an electrophoretic medium: and
a pump mechanism which can be connected to one end of each of the capillaries for filling the capillaries with the electrophoretic medium, the pump mechanism comprising:
a plunger for taking in or delivering the electrophoretic medium;
a slider which is bonded to one end of the plunger;
a linear motion system;
a compressed spring inserted between the slider and a junction of the linear motion system;
a cover which coaxially supports the slider, the spring and the junction so that the slider and the spring can move axially, the cover having one end fixed to the junction; and
detection means for detecting the position of the slider relative to the cover;
wherein:
the cover and the plunger move in one direction as one body when the electrophoretic medium is taken into the pump mechanism; and the spring pushes the plunger when the electrophoretic medium is injected into the capillaries, and
the detection means is constructed so that the detection object is detected when the slider has reached a position at which injection of the electrophoretic medium is to be completed.

5. A pump mechanism comprising:
a plunger for taking in or delivering an electrophoretic medium;
a slider which is bonded to one end of the plunger;
a linear motion system;
a compressed spring inserted between the slider and a junction of the linear motion system;
a cover which coaxially supports between the slider, the spring and the junction so that the slider and the spring can move axially the cover having one end fixed to the junction; and
detection means to detect the position of the slider relative to the cover;
wherein:
the cover and the plunger move in one direction as one body when the electrophoretic medium is taken in, and the spring pushes the plunger in the opposite direction when the electrophoretic medium is delivered, and
the detection means comprises a detection object bonded to the slider and a sensor to detect the position of the detection object.

6. A pump mechanism comprising:
a plunger for taking in or delivering an electrophoretic medium;
a slider which is bonded to one end of the plunger;
a linear motion system;
a compressed spring inserted between the slider and a junction of the linear motion system;
a cover which coaxially supports the slider, the spring and the junction so that the slider and the spring can move axially, the cover having one end fixed to the junction; and
detection means to detect the position of the slider relative to the cover;
wherein:
the cover and the plunger move in one direction as one body when the electrophoretic medium is taken in, and the spring pushes the plunger in the opposite direction when the electrophoretic medium is delivered, and
the detection means comprises: a slit plate which has slits spaced in the axial direction of the cover and is bonded to the slider; and an encoder which is attached to the cover to detect slits in the slit plate.

7. A pump mechanism comprising:
a plunger for taking in or delivering an electrophoretic medium;
a slider which is bonded to one end of the plunger;
a linear motion system;
a compressed spring inserted between the slider and a junction of the linear motion system;
a cover which coaxially supports the slider, the spring and the junction so that the slider and the spring can move axially, the cover having one end fixed to the junction; and
detection means to detect the position of the slider relative to the cover;
wherein:
the cover and the plunger move in one direction as one body when the electrophoretic medium is taken in, and the spring pushes the plunger in the opposite direction when the electrophoretic medium is delivered, and
the detection means is constructed so that the detection object is detected when the slider has reached a position at which polymer injection is to be completed.

* * * * *